June 7, 1966 O. O. DUNHAM Plant Pat. 2,643
CHRYSANTHEMUM PLANT
Filed Dec. 17, 1964
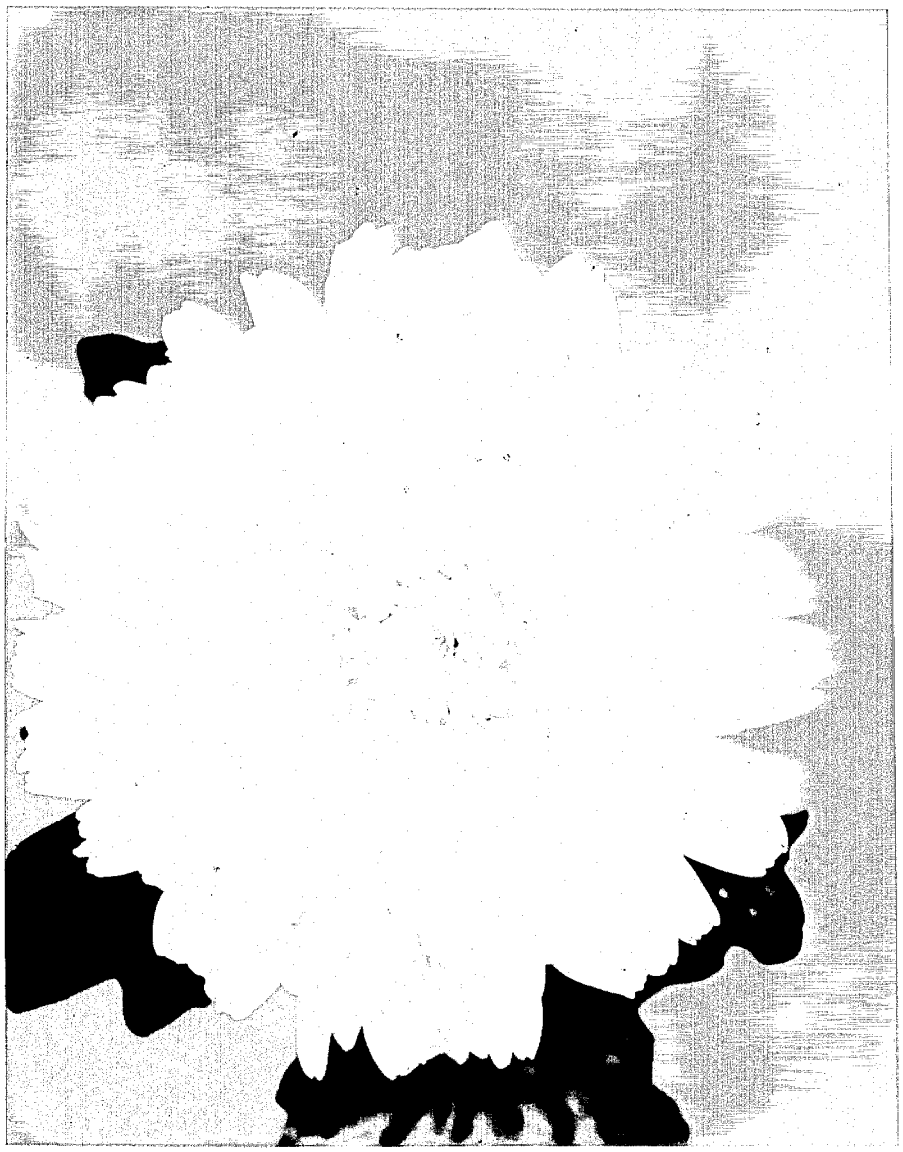
Inventor:
O. O. Dunham
by Robb & Robb
Attorneys

United States Patent Office

Plant Pat. 2,643
Patented June 7, 1966

2,643
CHRYSANTHEMUM PLANT

Orville O. Dunham, Niles, Mich., assignor to George J. Ball, Inc., West Chicago, Ill., a corporation of Illinois

Filed Dec. 17, 1964, Ser. No. 419,259
1 Claim. (Cl. Plt.—78)

My present invention comprises a new and distinct variety of chrysanthemum plant, the result of crossing the unpatented variety of my own origination which I designate as #56544 and the patented variety Plant Patent No. 2,006.

The object of my invention has been to produce an improved variety of chrysanthemum having many other desirable characteristics of so-called American Garden chrysanthemums together with the same kinds of characteristics from English Early chrysanthemums, the blossoms of this particular variety having an intense buttercup yellow aspect (Royal Horticultural Colour Chart).

My present new variety is essentially the result of hybridizing in a program which has been carried on for many years and involves the selection of certain of the characteristics of prior known varieties, largely of my own origination and which were developed as before stated from American Garden chrysanthemums and the English Early chrysanthemums, this program being characterized by careful selection and cross-breeding to produce new varieties of chrysanthemums, the parents having been selected so as to attempt to obtain the important and desirable characteristics of both with colors which would be acceptable from a commercial standpoint and distinct from prior known and produced varieties in commerce.

The result of the specific hybridization previously mentioned has been to produce this particular new and distinct variety of chrysanthemum plant which may in general be characterized as having intense buttercup yellow blooms, shorter, more compact, vigorous habit of growth, earlier, longer blooming period, greater profusion of bloom and better flower form.

The blooms of this new variety are of large size, the average in most cases when fully expanded being approximately 6" in diameter, the blooms being borne together and having very double petalage with petals too numerous to count. As grown in the vicinity of Niles, Michigan, the blooms appear on medium length, strong stems, averaging 12" to 15" in length.

The seed parent which is the un-named variety and which I number 56544 has transmitted its flower form to the instant variety, but in view of the fact that this particular variety is a late flowering type, it was crossed with the variety of Plant Patent No. 2,006 to give it earliness and this has resulted in production of flowers in the early part of September, usually by the 15th thereof.

The color and plant habit is better than the pollen parent, Plant Patent No. 2,006.

My new variety may be compared with other prior varieties such as those of Plant Patent Nos. 2,437 and 2,438, by stating that my new variety flowers earlier, has better color and plant habit than either of the prior mentioned varieties.

The early flowering as compared with the varieties of Plant Patent Nos. 2,437 and 2,438 is pointed out by stating that my new variety flowers at least 10 days earlier and sometimes prior thereto, the September 15 date previously mentioned having been usual.

The two prior varieties Plant Patent Nos. 2,437 and 2,438 also may be distinguished in that they tend to grow quite tall, attaining a height usually of 30" to 36", whereas the instant variety of my invention attains an approximate height of 15" to 20" usually, making it more desirable for garden border use.

My new variety has been asexually reproduced by cuttings in the vicinity of Niles, Michigan, and also near West Chicago, Illinois, where observations were made during the month of September upon which the description herein set forth subsequently in detail is based.

My new variety has been found to retain its distinctive characteristics through successive asexual reproduction.

The accompanying drawing forming a part hereof shows a typical bloom of my new variety, the colors being as nearly representative of the actual colors of the plant as is possible in such an illustration, the intense deep buttercup yellow contrasting substantially with the lighter yellow of the prior varieties of Plant Patent Nos. 2,437 and 2,438.

The color references are made based upon comparison with those in the Royal Horticultural Colour Chart.

*Description*

Parentage:
- *Seedling.*—Seed parent — #56544 — (unpatented). Pollen parent—Plant Patent No. 2,006.

Classification: Botanic—*Chrysanthemum indicum.*

*Flower*

Blooming habit: Blooms from early September profusely until a killing frost.

Bud:
- *Size.*—Large.
- *Form.*—Globular.
- Not materially affected by hot or wet weather.

Color:
- *When sepals first divide.*—Buttercup Yellow 5.
- *When petals begin to unfurl.*—Lemon Yellow 4.
- *When half blown.*—Inside of petals—Lemon Yellow 4. Reverse of petals—Aureolin 3/1.

Sepals: Smooth edge.

Calyx:
- *Shape.*—Funnel.
- *Size.*—Large and slender.
- *Aspect.*—Smooth.

Peduncle:
- *Length.*—Medium.
- *Aspect.*—Smooth.
- *Strength.*—Stiff and heavy.
- Bud opens well.

Bloom:
- *Size.*—Large.
- *Average size when fully expanded.*—About 6" in diameter.
- *Borne.*—Several together.
- *Stems.*—Medium and strong.
- *Form.*—When first open: Flat. Permanence: Retains its form to the end.
- *Petalage.*—Very double with innumerable petals under normal conditions.

Color:
- *Center of flower.*—Empire Yellow 603/1 tipped with 603.
- *Outer petals.*—Aureolin 3.
- *Base of petals (singlet).*—Aureolin 3/2.
- *Inside of petals.*—Lemon Yellow 4/1.
- *Reverse of petals.*—Aureolin 3/1.
- *General tonality from a distance.*—Buttercup Yellow 5/1.
- *Discoloration.*—General tonality at end of: First week—Buttercup Yellow 5/2. Third week—Lemon Yellow 4/2.

Petals:

*Texture.*—Thick.

After extended periods of wet weather the flower will rot.

*Appearance.*—Inside—satiny. Outside—shiny.

*Form.*—Pointed.

*Arrangement.*—Imbricated.

*Petaloids in center.*—Many.

*Persistence.*—Hang on and dry.

*Fragrance.*—None.

*Lastingness.*—On the plant—long. As cut flower—long.

Genital organs:

*Stamens, anthers.*—Small and many.

*Arrangement.*—Regular around styles.

*Stamens, filaments.*—Medium.

*Styles.*—Columnar and even. Length—medium and thin.

*Ovaries.*—Some protruding from calyx.

Plant:

*Form.*—Bush.

*Growth.*—Medium height and compact.

*Height.*—15" average.

*Spread.*—About 12".

Foliage:

*Size.*—Medium.

*Quantity.*—Normal,

*Shape.*—Lobed.

*Texture.*—Leathery.

*Ribs and veins.*—Prominent.

*Edge.*—Serrate.

*Serration.*—Single, large and deep.

*Stipules.*—Medium.

I claim:

A new and distinct variety of chrysanthemum plant substantially as herein disclosed, characterized as to novelty by the intense buttercup yellow color of its blooms, shorter, more compact vigorous habit of growth, earlier, longer blooming period, greater profusion of bloom and better flower form.

No references cited.

ABRAHAM G. STONE, *Primary Examiner.*